United States Patent [19]
Ingels

[11] Patent Number: 5,232,360
[45] Date of Patent: Aug. 3, 1993

[54] ORTHODONTIC PLIERS

[76] Inventor: Luis Ingels, 242 Irwindale, Azusa, Calif. 91702

[21] Appl. No.: 759,592

[22] Filed: Sep. 16, 1991

[51] Int. Cl.$^5$ .............................................. A61C 3/00
[52] U.S. Cl. ...................................... 433/4; 433/159; 81/416
[58] Field of Search .................... 433/4, 159, 160; 606/151, 157, 158; 29/268; 81/415, 416, 417; 294/99.2; 7/125; 403/348, 349

[56] References Cited

U.S. PATENT DOCUMENTS

| | | | |
|---|---|---|---|
| 680,119 | 8/1901 | Brewer, Jr. | 433/160 |
| 2,632,661 | 3/1953 | Cristofv | 81/416 |
| 3,982,450 | 9/1976 | Marsh | 81/416 |
| 4,536,958 | 8/1985 | Tosi | 81/416 |

FOREIGN PATENT DOCUMENTS 984590 7/1951 France ............................. 81/416

Primary Examiner—Cary E. O'Connor
Attorney, Agent, or Firm—Donald D. Mon

[57] ABSTRACT

Plier-like instruments for dental and medical use which can be readily disassembled for cleaning and sterilization and then quickly reassembled for use. No additional tools are needed for assembly and disassembly, and the manipulations are simple motions that may be accomplished even under sterile conditions wearing surgical gloves. The handles are spread apart to disengage circular segments of locking ribs on one handle with circular segments of channel and retaining lips on the other handle. A piloting shaft equipped with expanding spring ring maintains smooth, aligned operation of the instruments. There are no loose parts to manipulate in assembly or disassembly, and no additional tools are required.

4 Claims, 2 Drawing Sheets

ORTHODONTIC PLIERS

FIELD OF THE INVENTION

Plier type instruments for use in dental technology for fitting and adjusting orthodontic appliances and for other dental or surgical applications. These instruments utilize a swivel joint which can be quickly disassembled for clearing and sterilization.

BRIEF DESCRIPTION OF THE INVENTION

This invention provides pliers adapted with various types of jaws required for dental, medical, and surgical needs provided with a swivel joint connecting the handle members that can be disassembled quickly for cleaning and sterilization.

An object of this invention is to provide for quick disassembly of dental or medical pliers for cleaning and sterilization.

A further object of this invention is to provide quick disassembly of a swivel joint without the use of supplemental tools.

Another object of the invention is to provide a separable joint for dental or medical plier-like instruments without requiring loose parts for assembling the two basic handle members, and which can readily be sterilized.

In a preferred embodiment of the invention a protruding pin on the swivel axis of one handle engages in a bore on the matching swivel axis of the other plier handle. A resilient spring ring is provided on the pin to aid in retention of the pin in the bore. Channels in the body of the handle containing the bore are provided to receive and contain arcuate segments of protruding ribs on the other handle, all around the axis of rotation of the swivel joint connecting the plier handles. Disengaging the ribs from the channels by opening the pliers to the maximum permits withdrawal of the pin from the bore for disassembly.

The foregoing and other features and advantages of the invention will be fully understood from the following detailed description and the accompanying drawings, in which:

DETAILED DESCRIPTION OF THE INVENTION

Figure 1:
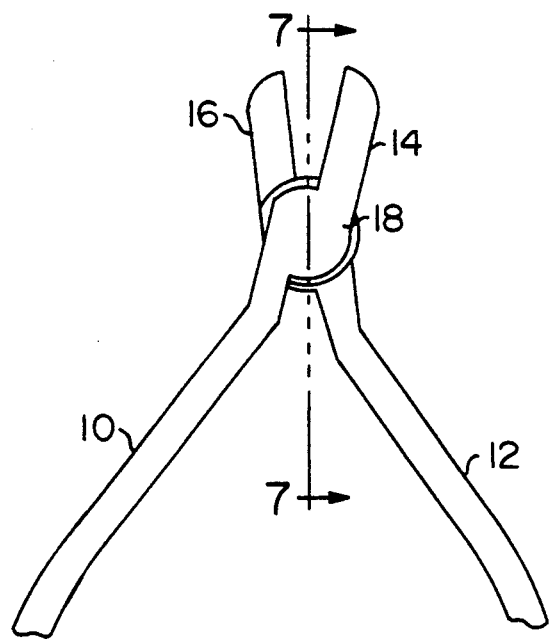
FIG. 1 is a plan view of a preferred embodiment of the invention.
Figure 2:
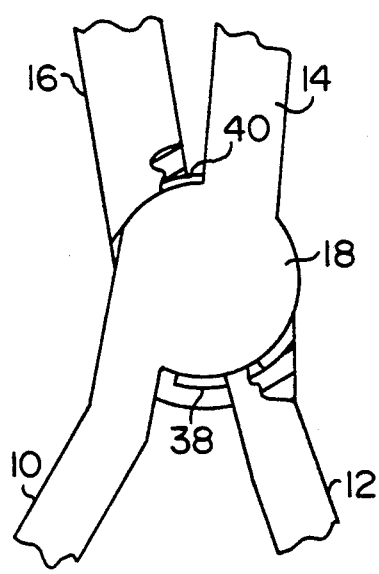
FIG. 2 is a plan view, partially in cutaway cross-section of the embodiment of FIG. 1.

A preferred embodiment of the invention is shown in FIG. 1. Details of the structure and arrangement of the parts of the embodiment of FIG. 1 are shown in FIGS. 2-6. It is to be understood that the length and shape of the handles and the working jaws of the pliers of this embodiment may be designed to fit the task for which the tool is to be used. It is well known in the art to design jaws as pin or ligature cutters, loop-forming pliers, distal cutters, wire-bending pliers, band removing pliers and numerous other types. In addition, handle lengths, off-sets and separations are varied for tasks, and are well-known in the art. The instruments of this invention are characterized by the swivel assembly which joins the two handle members 10 and 12.

Figure 7:
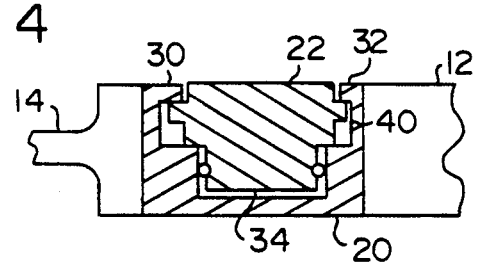
FIG. 7 is a fragmentary cross-section taken on line 7—7 of FIG. 1.

The jaw members 14 and 16 are connected integrally to the handle members 10 and 12 respectively by the swivel assembly 18. Each handle member has a reduced swivel section which combines with the other to form the total thickness of the tool which can be seen in FIG. 7 as swivel section 20 belonging to handle member 12, and swivel section 22 which is part of handle member 10.

Figure 3:
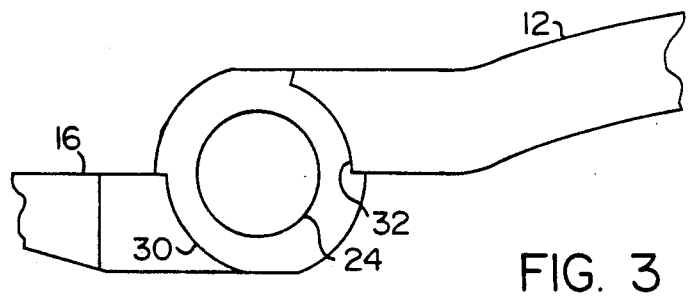
FIG. 3 is a plan view of a fragment of a disassembled handle of the embodiment of FIG. 1.
Figure 4:
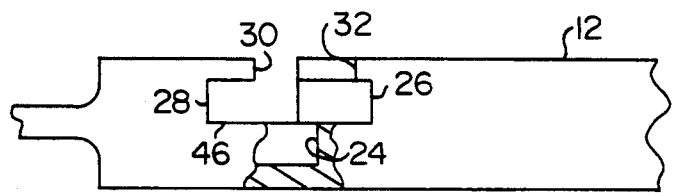
FIG. 4 is a fragmentary side elevation, partially in cross-section of the plan view in FIG. 3.

As can be seen in FIGS. 3 and 4, handle member 12 has a center swivel section 20 which has a blind bore 24 partially therethrough and under-cut channels 26 and 28 which are segments of cylindrical walls coaxial with bore 24, and which create over hanging lips 30 and 32 that are the same length as channel segments 26 and 28 and are likewise coaxial with bore 24 and are diametrically opposed. Channels 26 and 28 form a flat shoulder 46 which defines the thickness of the swivel 20.

Figure 5:
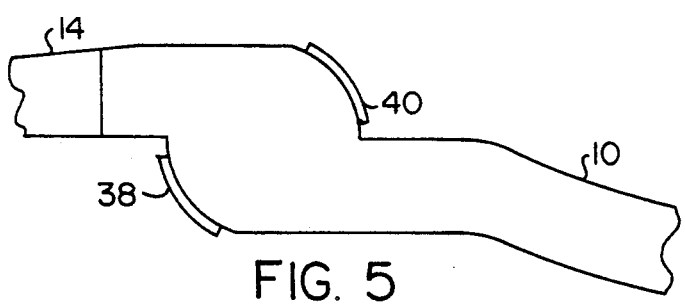
FIG. 5 is a plan view of a fragment of the second disassembled handle of the embodiment of FIG. 1.
Figure 6:
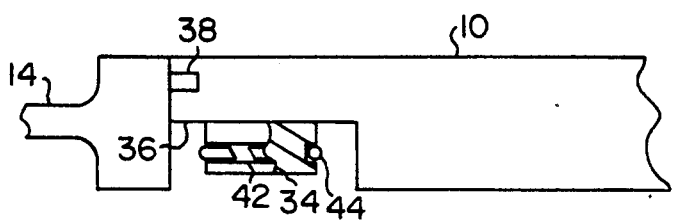
FIG. 6 is a fragmentary side elevation, partially in cross-section of the second disassembled handle of the plan view in FIG. 5.

In FIGS. 5 and 6 handle member 10 is shown with its swivel section 22 which has a cylindrical shaft 34 protruding from a counterbore face 36. Shaft 34 rotates around the axis of rotation of handle member 10. Protruding ribs 38 and 40 are segments of tubular cylinders radially opposed but coaxial with shaft 34. Shaft 34 has a peripheral annular groove 42 and a split spring ring 44 installed therein.

In the process of assembling the pliers after cleaning, the handles are held in their open position. Shaft 34 of handle 10 is pushed into bore 24 of handle 12 against the spring resistance of spring ring 44. In the most open position of handle members 10 and 12, the ribs 38 and 40 are free of engagement with over-hanging lips 30 and 32 of handle 12. When counter bore face 34 meets should 46 of handle 12, the handles 10 and 12 can be rotated toward each other to engage the protruding ribs 38 and 40 with the lips 30 and 32 of the channels 26 and 28, thereby holding the device in assembly for use. The working rotation of the instrument is essentially the length of engagement in rotation of the ribs 38 and 40 with the channels 26 and 28. Disassembly for cleaning and sterilization is the reverse of the above described process.

This invention is not to be limited to the embodiments described in the description and illustrated in the drawings, which are given by way of example and not of limitation, but only in accordance with the scope of the appended claims.

I claim:

1. Instrument pliers comprising:
    a first handle member and a second handle member joinable to rotate relative to one another around an axis of rotation, jaw means channel means and lip means on one of said members, and jaw means and rib means on the other of said members;
    a post on one of said handle members and a bore in the other of said handle members, and spring ring means around the post, said post and bore being centered on said central axis where the handle members are joined to one another, said ribs grooves and lips extending around said central axis for less than the full periphery thereof, whereby to hold the handle members together in a relatively closed position and to enable their separation when more widely spread apart;

said spring ring means making a resilient retention fit in said bore to hold the handle members together when they are more widely spread apart except upon the exertion of sufficient separative force to overcome the spring ring means when they are more widely spread apart.

2. Apparatus according to claim 1 in which said jaw means is provided with cutting edge means for severing materials.

3. Apparatus according to claim 1 in which said jaw means is provided with bending means for bending materials.

4. Apparatus according to claim 1 in which said jaw means is provided with holding means adapted for retention of materials.

* * * * *